US009308182B2

(12) United States Patent
Fitzer-Attas et al.

(10) Patent No.: US 9,308,182 B2
(45) Date of Patent: Apr. 12, 2016

(54) PARENTERAL FORMULATIONS OF RASAGILINE

(71) Applicants: Cheryl Fitzer-Attas, Dayton, NJ (US); Rom E Eliaz, Kadima (IL); Eran Blaugrund, Rehovot (IL); Aviva Gross, Kiryat Tivon (IL); Adi Mayk, Raanana (IL)

(72) Inventors: Cheryl Fitzer-Attas, Dayton, NJ (US); Rom E Eliaz, Kadima (IL); Eran Blaugrund, Rehovot (IL); Aviva Gross, Kiryat Tivon (IL); Adi Mayk, Raanana (IL)

(73) Assignee: TEVA PHARMACEUTICAL INDUSTRIES, LTD., Petach-Tikva (IL)

( * ) Notice: Subject to any disclaimer, the term of this patent is extended or adjusted under 35 U.S.C. 154(b) by 0 days.

(21) Appl. No.: 13/969,295

(22) Filed: Aug. 16, 2013

(65) Prior Publication Data

US 2014/0051767 A1 Feb. 20, 2014

Related U.S. Application Data

(60) Provisional application No. 61/684,530, filed on Aug. 17, 2012, provisional application No. 61/775,318, filed on Mar. 8, 2013.

(51) Int. Cl.
*A61K 31/135* (2006.01)
*A61K 9/00* (2006.01)

(52) U.S. Cl.
CPC .............. *A61K 31/135* (2013.01); *A61K 9/0004* (2013.01); *A61K 9/0019* (2013.01)

(58) Field of Classification Search
USPC ....................................................... 514/657
See application file for complete search history.

(56) References Cited

U.S. PATENT DOCUMENTS

| | | | |
|---|---|---|---|
| 5,387,612 A | 2/1995 | Youdim et al. | |
| 5,453,446 A | 9/1995 | Youdim et al. | |
| 5,457,133 A | 10/1995 | Youdim et al. | |
| 5,486,541 A | 1/1996 | Sterling et al. | |
| 5,519,061 A | 5/1996 | Youdim et al. | |
| 5,532,415 A | 7/1996 | Youdim et al. | |
| 5,576,353 A | 11/1996 | Youdim et al. | |
| 5,599,991 A | 2/1997 | Youdim et al. | |
| 5,668,181 A | 9/1997 | Youdim et al. | |
| 5,744,500 A | 4/1998 | Youdim et al. | |
| 5,786,390 A | 7/1998 | Youdim et al. | |
| 5,891,923 A | 4/1999 | Youdim et al. | |
| 6,126,968 A | 10/2000 | Peskin et al. | |
| 6,277,886 B1 | 8/2001 | Levy et al. | |
| 6,309,634 B1 * | 10/2001 | Bankiewicz et al. | 424/93.2 |
| 6,316,504 B1 | 11/2001 | Youdim et al. | |
| 6,462,222 B1 | 10/2002 | Chorev et al. | |
| 6,630,514 B2 | 10/2003 | Youdim et al. | |
| 6,956,060 B2 | 10/2005 | Youdim et al. | |
| 7,396,860 B2 | 7/2008 | Blaugrund et al. | |
| 7,491,847 B2 | 2/2009 | Frenkel | |
| 7,547,806 B2 | 6/2009 | Frenkel et al. | |
| 7,572,834 B1 | 8/2009 | Sterling et al. | |
| 7,598,420 B1 | 10/2009 | Sterling et al. | |
| 7,619,117 B1 | 11/2009 | Lidor-Hadas et al. | |
| 7,750,051 B2 | 7/2010 | Frenkel et al. | |
| 7,815,942 B2 | 10/2010 | Peskin | |
| 7,855,233 B2 | 12/2010 | Frenkel et al. | |
| 7,968,749 B2 | 6/2011 | Frenkel et al. | |
| 8,080,584 B2 | 12/2011 | Safadi et al. | |
| 8,143,315 B2 | 3/2012 | Stahl et al. | |
| 8,334,409 B2 | 12/2012 | Frenkel | |
| 8,569,379 B2 | 10/2013 | Petit et al. | |
| 8,614,252 B2 | 12/2013 | Frenkel et al. | |
| 8,691,872 B2 | 4/2014 | Lorimer et al. | |
| 8,809,310 B2 | 8/2014 | Poewe | |
| 8,946,300 B2 | 2/2015 | Blaugrund et al. | |
| 8,946,482 B2 | 2/2015 | Thyrann et al. | |
| 2002/0169187 A1 * | 11/2002 | Svensson | 514/318 |
| 2004/0127577 A1 | 7/2004 | Blaugrund et al. | |
| 2006/0018957 A1 | 1/2006 | Lerner et al. | |
| 2006/0094783 A1 | 5/2006 | Youdim | |
| 2006/0188581 A1 | 8/2006 | Peskin | |
| 2007/0100001 A1 | 5/2007 | Youdim et al. | |
| 2007/0112217 A1 | 5/2007 | Frenkel et al. | |
| 2007/0232700 A1 * | 10/2007 | Blaugrund et al. | 514/629 |
| 2009/0062400 A1 | 3/2009 | Oron et al. | |
| 2009/0076160 A1 | 3/2009 | Lendvai et al. | |
| 2009/0111892 A1 | 4/2009 | Patashnik et al. | |
| 2009/0181086 A1 | 7/2009 | Safadi et al. | |
| 2009/0312436 A1 | 12/2009 | Levy et al. | |
| 2010/0008983 A1 | 1/2010 | Safadi et al. | |
| 2010/0137447 A1 | 6/2010 | Lehmann et al. | |

(Continued)

FOREIGN PATENT DOCUMENTS

WO WO 2007/060491 * 5/2007
WO WO 2007/098264 * 8/2007

(Continued)

OTHER PUBLICATIONS

Kyoko Goto et al.Psychiatry and Clinical Neurosciences (2000), 54, 507-511.*
Perkins et al. (2004) The use of Mini-Osmotic Pumps in continuous infusion Studies.*
Guerreiro et al (Arg Neuropsiquitr 2010; 68(6):869-872).*
WebMD (2004, 1-3).*
U.S. Appl. No. 12/283,022, filed Sep. 8, 2008, Lidor-Hadas et al.
U.S. Appl. No. 12/283,105, filed Sep. 8, 2008, Sterling et al.
U.S. Appl. No. 12/283,107, filed Sep. 8, 2008, Sterling et al.

(Continued)

*Primary Examiner* — Shirley V Gembeh
(74) *Attorney, Agent, or Firm* — John P. White; Gary J. Gershik; Cooper & Dunham LLP

(57) ABSTRACT

This application provides a method of preferentially inhibiting monoamine oxidase A (MAOA) in the brain of a subject relative to in the intestine of the subject comprising parenterally administering to the subject a controlled release formulation comprising a therapeutically effective amount of rasagiline or a pharmaceutically acceptable salt thereof.

19 Claims, 3 Drawing Sheets

(56) References Cited

U.S. PATENT DOCUMENTS

| | | |
|---|---|---|
| 2010/0168239 A1 | 7/2010 | Poewe |
| 2010/0189788 A1 | 7/2010 | Safadi et al. |
| 2010/0189790 A1 | 7/2010 | Safadi et al. |
| 2010/0189791 A1 | 7/2010 | Safadi et al. |
| 2011/0130466 A1 | 6/2011 | Lorenzl |
| 2011/0152381 A1 | 6/2011 | Frenkel et al. |
| 2011/0313050 A1 | 12/2011 | Rimkus et al. |
| 2012/0003310 A1 | 1/2012 | Safadi et al. |
| 2012/0059058 A1 | 3/2012 | Lorimer et al. |
| 2012/0100189 A1 | 4/2012 | Safadi et al. |
| 2012/0101168 A1 | 4/2012 | Bahar et al. |
| 2012/0238636 A1 | 9/2012 | Patashnik et al. |
| 2012/0263789 A1 | 10/2012 | Safadi et al. |
| 2012/0301542 A1 | 11/2012 | Sela et al. |
| 2013/0089610 A1 | 4/2013 | Safadi et al. |
| 2013/0089611 A1 | 4/2013 | Ulanenko et al. |
| 2013/0089612 A1 | 4/2013 | Safadi et al. |
| 2013/0345310 A1 | 12/2013 | Rimkus et al. |
| 2014/0072526 A1 | 3/2014 | Lehmann et al. |
| 2014/0364506 A1 | 12/2014 | Bahar et al. |

FOREIGN PATENT DOCUMENTS

| | | |
|---|---|---|
| WO | WO 2010/070090 | 6/2010 |
| WO | WO 2011/003938 | 1/2011 |
| WO | WO 2011/095973 | 8/2011 |

OTHER PUBLICATIONS

U.S. Appl. No. 13/651,307, filed Oct. 12, 2012, Levy et al.
U.S. Appl. No. 13/859,625, filed Apr. 9, 2013, Levy et al.
U.S. Appl. No. 13/967,240, filed Aug. 14, 2013, Rimkus et al.
U.S. Appl. No. 14/016,960, filed Sep. 3, 2013, Lehmann et al.
U.S. Appl. No. 14/092,526, filed Nov. 27, 2013, Levy et al.
U.S. Appl. No. 14/139,212, filed Dec. 23, 2013, Safadi et al.
Written Opinion of the International Searching Authority for International Application No. PCT/US13/55404, issued Dec. 30, 2013.
International Search Report of the International Searching Authority for International Application No. PCT/US13/55404, issued Jan. 16, 2014.
Cadario, B (2008), "Drug information perspectives: Rasagiline," British Columbia Drug and Poison Information Center, Vancouver 8(3):1-8.
Youdim MBH, et al., "Rasagiline (N-propargyl-1R(+)-aminoindan), a selective and potent inhibitor of mitochondrial monoamine oxidase B", Br. J. Pharmacol., 2001, 132:500-6.
U.S. Appl. No. 14/458,410, filed Aug. 13, 2014, Patashnik et al.
U.S. Appl. No. 14/459,877, filed Aug. 14, 2014, Anton Frenkel and Tamas Koltai.

\* cited by examiner

PARENTERAL FORMULATIONS OF RASAGILINE

This application claims benefit of U.S. Provisional Application No. 61/775,318, filed Mar. 8, 2013, and U.S. Provisional Application No. 61/684,530, filed Aug. 17, 2012, the entire content of each of which is hereby incorporated by reference herein.

Throughout this application various publications are referenced. The disclosures of these publications in their entireties are hereby incorporated by reference into this application in order to more fully describe the state of the art to which this invention pertains.

BACKGROUND

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514, 7,750,051, and 7,855,233 disclose R(+)-N-propargyl-l-aminoindan ("R-PAI"), also known as rasagiline, and its pharmaceutically acceptable salts. These U.S. patents also disclose that rasagiline is a selective inhibitor of the B-form of the enzyme monoamine oxidase ("MAO-B") and is useful in treating Parkinson's disease and various other conditions by inhibition of MAO-B in the brain.

U.S. Pat. Nos. 6,126,968, 7,572,834, and 7,598,420, U.S. patent application Ser. Nos. 12/283,022, and 12/283,107 and PCT publications WO 95/11016 and WO 2006/014973, hereby incorporated by reference, disclose pharmaceutical compositions comprising rasagiline and processes for their preparation.

AZILECT® is a commercially available rasagiline mesylate immediate release formulation indicated for the treatment of the signs and symptoms of idiopathic Parkinson's disease as initial monotherapy and as adjunct therapy to levodopa. The current marketed formulation of rasagiline (Azilect®) is rapidly absorbed, reaching peak plasma concentration ($t_{max}$) in approximately 1 hour. The absolute bioavailability of rasagiline is about 36%. (AZILECT® Product Label, May 2006).

A concern in using monoamine oxidase ("MAO") inhibitors is the risk of hypertensive crises, often called the "cheese effect." (Simpson, G. M. and White K. "Tyramine studies and the safety of MAOI drugs." J Clin Psychiatry. 1984 July; 45 (7 pt 2): 59-91.) This effect is caused by inhibition of peripheral MAO. A high concentration of peripheral MAO is found in the stomach.

Rasagiline is a nonspecific inhibitor of MAOA, and has been shown to inhibit MAOA activity in the brain and liver of rats. Youdim M, Gross A, Finberg J, "Rasagiline [N-propargyl-1R(+)-aminoindan], a selective and potent inhibitor of mitochondrial monoamine oxidase B", Br. J. Pharm. 132: 500-506 (2001).

SUMMARY OF THE INVENTION

This invention provides a method of preferentially inhibiting monoamine oxidase A (MAOA) in the brain of a subject relative to in the intestine of the subject comprising parenterally administering to the subject a formulation comprising a therapeutically effective amount of rasagiline or a pharmaceutically acceptable salt thereof.

This invention also provides a method of method of treating a subject in need of rasagiline therapy comprising parenterally administering to the subject a formulation comprising a therapeutically effective amount of rasagiline or a pharmaceutically acceptable salt thereof, so as to thereby treat the subject.

This invention also provides the use of a controlled release formulation of rasagiline or a pharmaceutically acceptable salt thereof for the preparation of a medicament to preferentially inhibit MAOA in the brain of a subject relative to in the intestine of the subject, or to treat a subject in need of rasagiline therapy.

This invention also provides a controlled release formulation of rasagiline or a pharmaceutically acceptable salt thereof for use in preferentially inhibiting MAOA in the brain of a subject relative to in the intestine of the subject, or to treat a subject in need of rasagiline therapy.

BRIEF DESCRIPTION OF THE FIGURES

FIG. 2 shows that all groups gained about 6-9% except the group of 0.8 mg/kg/day delivered by ALZET® pumps, in which the weight gain was lower (1.3%).

DETAILED DESCRIPTION OF THE INVENTION

Figure 1:
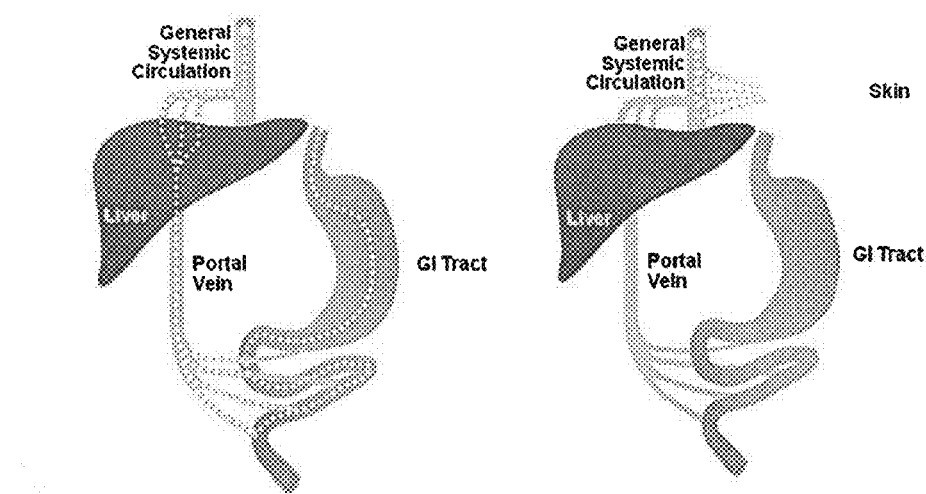
FIG. 1: Diagram illustrating the first-pass effect and delivery options that avoid first-pass metabolism

R(+)-N-propargyl-l-aminoindan ("R-PAI"), also known as rasagiline, is a small molecule having the following chemical structure:

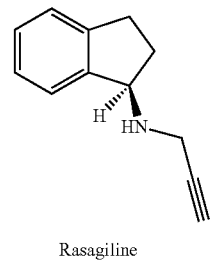

Rasagiline

Rasagiline has been reported to be a selective inhibitor of the B-form of the enzyme monoamine oxidase ("MAO-B") and is useful in treating Parkinson's disease and various other conditions by inhibition of MAO-B in the brain.

A pharmaceutically acceptable salt of rasagiline, rasagiline citrate, and the process of preparing the same has been described in U.S. Pat. No. 7,855,233, the entire content of which is hereby incorporated by reference.

Crystalline rasagiline, and the process of preparing the same has been described in U.S. Pat. Nos. 7,750,051, 7,968, 749, the entire contents of which are hereby incorporated by reference.

Delayed release rasagiline formulations have been described in United States Application Publication Nos. 2009/0181086, 2010/0189790, 2010/0189788, 2010/0189787, and 2010/0189791, the entire content of each of which is hereby incorporated by reference.

This invention provides a method of preferentially inhibiting monoamine oxidase A (MAOA) in the brain of a subject relative to in the intestine of the subject comprising parenterally administering to the subject a formulation comprising a therapeutically effective amount of rasagiline or a pharmaceutically acceptable salt thereof.

In one embodiment, the therapeutically effective amount of rasagiline or a pharmaceutically acceptable salt thereof is delivered substantially entirely into the bloodstream of the subject so as to reduce or avoid intestinal inhibition of MAOA while enhancing MAOA inhibition in the brain of the subject.

In one embodiment, the subject is in need of rasagiline therapy.

In one embodiment, the formulation is a controlled release formulation.

In one embodiment, rasagiline is rasagiline base.

In one embodiment, the pharmaceutically acceptable salt is citrate, tannate, malate, mesylate, maleate, fumarate, tartrate, esylate, p-toluenesulfonate, benzoate, acetate, phosphate or sulfate.

This invention also provides a method of treating a subject in need of rasagiline therapy comprising parenterally administering to the subject a formulation comprising a therapeutically effective amount of rasagiline or a pharmaceutically acceptable salt thereof, so as to thereby treat the subject.

In one embodiment, the formulation is a controlled release formulation.

In one embodiment, rasagiline is rasagiline base.

In one embodiment, the pharmaceutically acceptable salt is citrate, tannate, malate, mesylate, maleate, fumarate, tartrate, esylate, p-toluenesulfonate, benzoate, acetate, phosphate or sulfate.

In one embodiment, the subject in need of rasagiline therapy is a subject afflicted with Parkinson's Disease. In another embodiment, the subject in need of rasagiline therapy is a subject afflicted with premotor Parkinson's Disease. In another embodiment, the subject in need of rasagiline therapy is a subject afflicted with attention deficit hyperactivity disorder (ADHD), bipolar disorder, depression, post-traumatic stress disorder (PTSD), multiple system atrophy (MSA), Progressive Supranuclear Palsy (PSP) or amyotrophic lateral sclerosis (ALS). In another embodiment, the subject in need of rasagiline therapy is a subject afflicted with restless legs syndrome, hearing loss, glaucoma, or olfactory dysfunction. In another embodiment, the subject in need of rasagiline therapy is a subject afflicted with Parkinson's Disease, Multiple Sclerosis (MS), Alzheimer's Disease, Amyotrophic Lateral Sclerosis (ALS) or Huntington's Disease (HD). In another embodiment, the subject in need of rasagiline therapy is a subject afflicted with depression.

In one embodiment, the percentage of MAOA inhibition in the brain is at least 5% higher than for a corresponding oral dose. In another embodiment, the percentage of MAOA inhibition in the brain is at least 6% higher than for a corresponding oral dose. In another embodiment, the percentage of MAOA inhibition in the brain is at least 7% higher than for a corresponding oral dose.

In one embodiment, the percentage of MAOA inhibition in the brain is at least 10% higher than the percentage of MAOA inhibition in the intestine. In another embodiment, the percentage of MAOA inhibition in the brain is at least 20% higher than the percentage of MAOA inhibition in the intestine. In another embodiment, the percentage of MAOA inhibition in the brain is at least 30% higher than the percentage of MAOA inhibition in the intestine. In another embodiment, the percentage of MAOA inhibition in the brain is at least 40% higher than the percentage of MAOA inhibition in the intestine.

In one embodiment, the controlled release formulation is a subcutaneous osmotic pump.

In one embodiment, the controlled release formulation releases rasagiline or a pharmaceutically acceptable salt thereof at a rate of 0.25 µl/hr-10.0 µl/hr. In another embodiment, the controlled release formulation releases rasagiline or a pharmaceutically acceptable salt thereof at a rate of about 0.5 µl/hr.

In one embodiment, the controlled release formulation comprises rasagiline at a daily dosage of 0.003 mg/kg-0.13 mg/kg. In another embodiment, the controlled release formulation releases rasagiline at a daily dosage of about 0.016 mg/kg.

In one embodiment, the controlled release formulation contains a total amount of rasagiline for a course of therapy lasting 1 week to 6 months. In another embodiment, the controlled release formulation contains a total amount of rasagiline for a course of therapy lasting 1 week. In one embodiment, the controlled release formulation contains a total amount of rasagiline for a course of therapy lasting 1 week to 6 months. In another embodiment, the controlled release formulation contains a total amount of rasagiline for a course of therapy lasting 2 weeks. In one embodiment, the controlled release formulation contains a total amount of rasagiline for a course of therapy lasting 1 week to 6 months. In another embodiment, the controlled release formulation contains a total amount of rasagiline for a course of therapy lasting 4 weeks. In one embodiment, the controlled release formulation contains a total amount of rasagiline for a course of therapy lasting 1 week to 6 months. In another embodiment, the controlled release formulation contains a total amount of rasagiline for a course of therapy lasting 2 months. In one embodiment, the controlled release formulation contains a total amount of rasagiline for a course of therapy lasting 1 week to 6 months. In another embodiment, the controlled release formulation contains a total amount of rasagiline for a course of therapy lasting 4 months. In one embodiment, the controlled release formulation contains a total amount of rasagiline for a course of therapy lasting 1 week to 6 months. In another embodiment, the controlled release formulation contains a total amount of rasagiline for a course of therapy lasting 6 months.

In one embodiment, the subject is human.

This invention also provides a controlled release parenteral formulation comprising rasagiline or a pharmaceutically acceptable salt thereof.

In one embodiment, the controlled release parenteral formulation is an osmotic pump.

In one embodiment, the controlled release parenteral formulation is a subcutaneous osmotic pump, vaginal ring, or vaginal cream.

This invention also provides the use of a controlled release formulation of rasagiline or a pharmaceutically acceptable salt thereof for the preparation of a medicament to preferentially inhibit MAOA in the brain of a subject relative to in the intestine of the subject, or to treat a subject in need of rasagiline therapy.

This invention also provides a controlled release formulation of rasagiline or a pharmaceutically acceptable salt thereof for use in preferentially inhibiting MAOA in the brain of a subject relative to in the intestine of the subject, or to treat a subject in need of rasagiline therapy.

For the foregoing embodiments, each embodiment disclosed herein is contemplated as being applicable to each of the other disclosed embodiments.

Terms

As used herein, and unless stated otherwise, each of the following terms shall have the definition set forth below.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

As used herein, a "controlled release" of an agent refers to the release of the agent at a predetermined rate over time.

As used herein, an osmotic pump refers to a drug form or formulation which releases an agent at a controlled, and usually predetermined, rate using osmotic pressure.

As used herein, a "subject in need of rasagiline therapy" means a subject suffering from any condition for which rasagiline has a therapeutic benefit. Such conditions include, but are not limited to, Parkinson's Disease, premotor Parkinson's Disease, amyotrophic lateral sclerosis, restless legs syndrome (RLS), multiple system atrophy (MSA), hearing loss, glaucoma, olfactory dysfunction, Progressive Supranuclear Palsy (PSP), attention deficit hyperactivity disorder (ADHD), bipolar disorder, depression, or post-traumatic stress disorder (PTSD). U.S. Pat. Nos. 6,126,968; U.S. Pat. No. 7,396,860; U.S. Ser. No. 11/731,493; U.S. Ser. No. 12/223,794; U.S. Pat. No. 8,188,149; U.S. Ser. No. 12/231,601; U.S. Ser. No. 13/192,019; U.S. Ser. No. 12/456,166.

As used herein, "rasagiline" means rasagiline base or a pharmaceutically acceptable salt thereof.

A "salt" is salt of the instant compounds which have been modified by making acid or base salts of the compounds. The term "pharmaceutically acceptable salt" in this respect, refers to the relatively non-toxic, inorganic and organic acid or base addition salts of compounds of the present invention.

As used herein, a "pharmaceutically acceptable salt" of rasagiline includes citrate, tannate, malate, mesylate, maleate, fumarate, tartrate, esylate, p-toluenesulfonate, benzoate, acetate, phosphate and sulfate salts. For the preparation of pharmaceutically acceptable acid addition salts of the compounds of the invention, the free base can be reacted with the desired acids in the presence of a suitable solvent by conventional methods.

Rasagiline can also be used in its free base form. A process of manufacture of the rasagiline free base is described in U.S. Pat. Nos. 7,750,051 and 7,968,749, the contents of which are hereby incorporated by reference.

As used herein, "administering to the subject" means the giving of, dispensing of, or application of medicines, drugs, or remedies to a subject to relieve or cure a pathological condition. Oral administration is one way of administering the instant compounds to the subject.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat a symptom of a disorder or disease without causing undue adverse side effects. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, "drug substance" refers to the active ingredient in a drug product, which provides pharmacological activity or other direct effect in the diagnosis, cure, mitigation, treatment, or prevention of disease, or to affect the structure or any function of the body of man or animals.

As used herein, "drug product" refers to the finished dosage form containing the drug substance as well as at least one pharmaceutically acceptable carrier.

A dosage unit may comprise a single compound or mixtures of compounds thereof. A dosage unit can be prepared for oral dosage forms, such as tablets, capsules, pills, powders, and granules.

As used herein, a "pharmaceutically acceptable" carrier or excipient is one that is suitable for use with humans and/or animals without undue adverse side effects (such as toxicity, irritation, and allergic response) commensurate with a reasonable benefit/risk ratio.

As used herein, to "treat" or "treating" encompasses, e.g., inducing inhibition, regression, or stasis of the disorder and/or disease. As used herein, "inhibition" of disease progression or disease complication in a subject means preventing or reducing the disease progression and/or disease complication in the subject.

As used herein, "about" in the context of a numerical value or range means ±10% of the numerical value or range recited or claimed.

It is understood that where a parameter range is provided, all integers within that range, and hundredth thereof, are also provided by the invention. For example, "0.25-2.0 mg/day" includes 0.25 mg/day, 0.26 mg/day, 0.27 mg/day, etc. up to 2.0 mg/day.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Introduction

MAOA is the natural barrier to indirect sympathomimetic amines such as tyramine, which act by releasing norepinephrine (NE) from nerve endings, which may cause a malignant increase in blood pressure (the "cheese effect"). MAOA is important for the catabolism of tyramine which is ingested in certain foods.

Due to the first pass metabolism of drugs which are delivered orally, there are benefits of the parenteral administration of drugs (e.g. subcutaneous delivery in the form of patch). The first-pass effect is illustrated in FIG. 1. The blood from the intestine, stomach, pancreas and other close organs, is drained through the portal vein to the liver. In the liver, which contains both MAOA and MAOB enzymes, tyramine is catabolized by oxidative deamination to inert metabolites. Only small amount of tyramine, which didn't affect blood pressure, reach the hepatic vein and the systemic circulation. In case of MAO inhibition by rasagiline, larger doses of tyramine (which were not catabolyzed in the intestine and liver), will reach systemic circulation and cause the "cheese effect". The first pass metabolism limits the oral bioavailability of highly metabolized drugs. Rasagiline itself is metabolized to aminoindan (which does not inhibit MAO) by the enzymes of the cytochrom P450 family. By omitting the first pass metabolism. Larger amounts of rasagiline may enter the brain, causing more pronounced brain MAO inhibition.

Rand et al. demonstrated the importance of MAOA enzymes, both in the intestine and the liver in creating the cheese effect with tyramine. Tyramine at 1 mg, injected systematically, causes an increase of 59 mmHg in blood pressure. The same amount of tyramine injected into the portal vein, which enters the liver, causes an increase in blood pressure of only 18 mmHg. M. J. Rand, J. Wilson, Mechanisms of the pressor and depressor actions of St 155 (2-(2,6-dichlorophenylamino)-2-imidazoline hydrochloride, catapres®), European Journal of Pharmacology, Volume 3, Issue 1, April 1968, Pages 27-33, ISSN 0014-2999, 10.1016/0014-2999 (68)90044-7. This is due to the fact that most of the tyramine is catabolized by the liver MAO enzymes. Eviscerated rats, which had the entire gastrointestinal tract removed were unable to prevent the increase the blood pressure of tyramine. Finally nialamide (a non specific MAO inhibitor) caused an severe increase in blood pressure in all the treatment groups, proving the importance of free MAOA for catabolism of tyramine.

Materials and Methods

Rasagiline was administered to male Sprague Dawely rats, 6 in a group, using ALZET® osmotic minipumps model 2002 (DURECT Corporation, Cupertino, Calif. 95014). ALZET® osmotic minipumps are described in Perkins L, Peer C, and Murphy-Hackley P. "Chapter 21: The use of mini-osmotic pumps in continuous infusion studies" in *Handbook of Pre-Clinical Continuous Intravenous Infusion*, (Smith & Healing, eds., Taylor and Francis, 2000), the contents of which are incorporated herein by reference.

The ALZET® osmotic minipumps used release rasagiline at a rate of 0.5 μl/hour over two weeks. Rasagiline concentrations in the pumps were calculated in order to deliver daily doses of 0, 0.02, 0.05, 0.1, 0.2, 0.4 and 0.8 mg/kg rasagiline salt (0, 0.013, 0.032, 0.064, 0.13, 0.26 and 0.52 base). For comparison, similar daily doses of rasagiline were given by oral administration (2 ml/kg). Each route of administration had its own control (saline) group.

Implantation of Minipumps

Rats were anesthetized in a chamber with 4% Isoflurane. During surgical procedure anesthesia was maintained by a homemade nose cone with 1.5% Isoflurane.

The osmotic minipumps were inserted subcutaneously with a single surgical procedure: after clipping the fur from the dorsal area and cleaning the skin with antiseptic skin preparation, about 1 cm long incision was made on the dorsum of the animal, midway between both scappulae. The pump was placed along the axis of the body to one side of the backbone. The incision was positioned about 1-2 cm caudal to the estimated caudal end of the minipump when it is in place.

A pair of hemostats was inserted through the incision under the skin in a cranial direction and the jaws of the hemostats opened to make a subcutaneous pocket for the minipump. The pump was inserted into the subcutaneous pocket and the skin sutured.

Preparation of Organs for MAO Activity

After two weeks of treatment the animals were sacrificed. From each rat, brain (half) and a part of liver were dissected and frozen. The intestine was excised about ½ cm below the stomach about 1-2 cm long, washed with sucrose 0.32 Molar and frozen at −70° C.

Method of MAO Activity Determination

Tissue homogenates were pre incubated (37° C.) in the presence of clorgyline or deprenyl to inhibit the activity of MAO-A or MAO-B respectively. For MAO-B determination, samples were incubated for 20 minutes with $C^{14}$ PEA 10 μM and for MAO-A determination samples were incubated 30 minutes with $C^{14}$ −5HT 100 μM as substrate Termination of the reaction was done by acidification. The labeled metabolites were extracted into toluene:ethyl acetate, and counted in a β counter. Percent of inhibition was calculated using the average dpm of the control group as 100% activity, by the formula:

% inhibition=100−(100*dpm dose/dpm control)

Example 1

Weight Change

Figure 2:
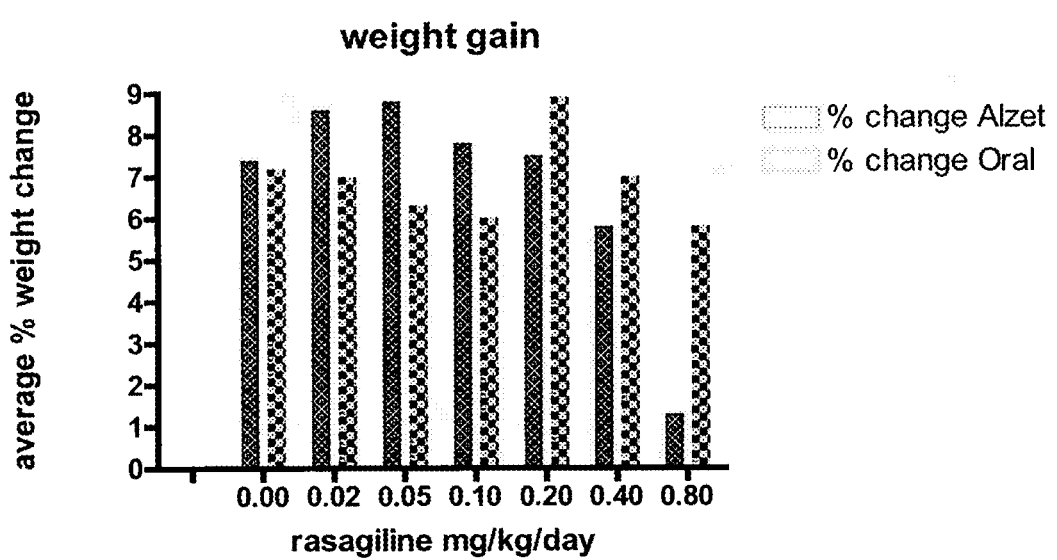
FIG. 2: ALZET® pumps groups were weighed on the first and last day of the study. The oral administered groups were weighed on the first day and also on day 6 and 13 of the study.
Figure 3:
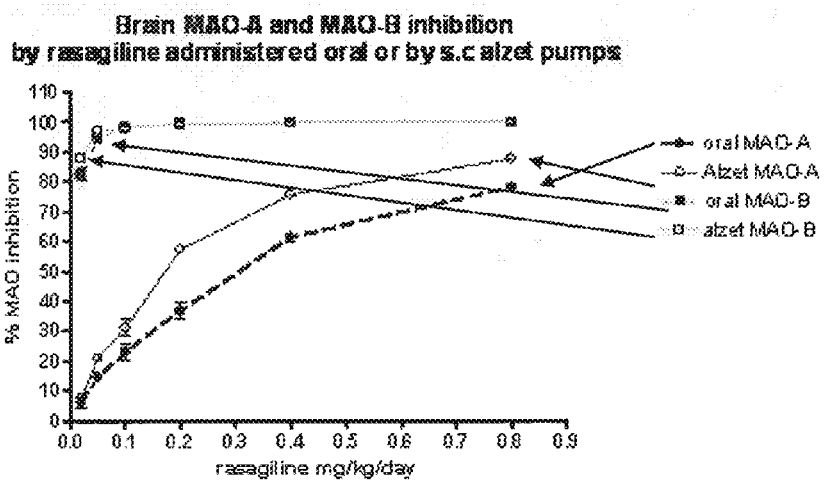
FIG. 3 The dose-dependent inhibition of MAOA and MAOB activity by rasagiline administered by oral and subcutaneous ALZET® pump is shown in different tissues.
Figure 3:
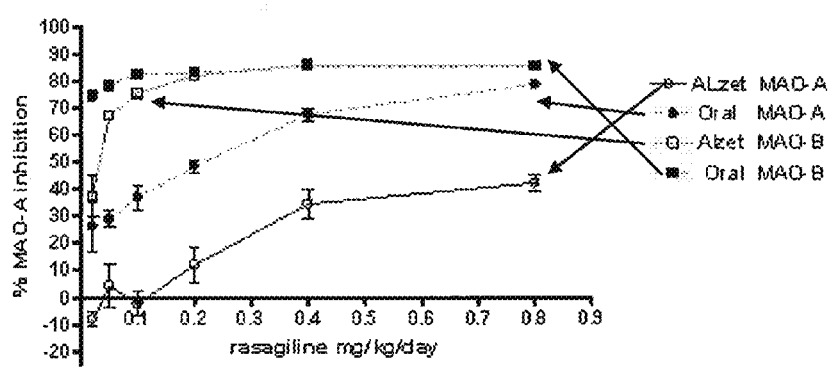
Figure 3:
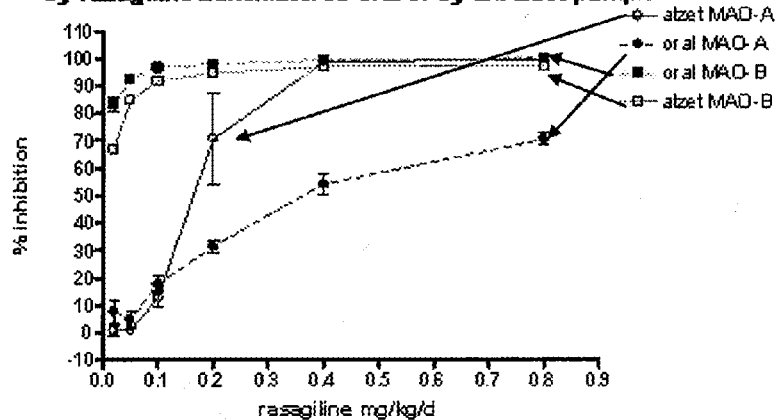

ALZET® pumps groups were weighed on the first and last day of the study. The oral administered groups were weighed on the first day and also on day 6 and 13 of the study. The percent weight changes is presented in FIG. 2, which shows that all groups gained about 6-9% in weight except the group of 0.8 mg/kg/day delivered by ALZET® pumps, in which the weight gain was lower (1.3%).

Example 2

MAO-Inhibition

The results of MAO activity (dpm+/−sd) are presented in Table 1 and percent of MAO inhibition are presented in Table 2. Inhibition curves for MAO from each tissue (% inhibition+/−sd) are presented for each tissue. The doses used caused full MAO-B inhibition (97-100%) in the brain and liver by both routes of administration.

In the intestine the maximal MAO-B inhibition was about 85% by both routes. At the lower concentration of 0.02 mg/kg/day (salt) given orally, intestinal MAO-B activity was already inhibited by a level of 74% while with the pumps this dose caused only 37% inhibition.

MAO-A Inhibition was Dose Dependent in all Tissues

In the intestine, the three lowest doses of 0.02-0.1 mg/kg/day (salt) did not inhibit MAO-A when given by pumps. These doses caused 26-37% inhibition when given orally.

A level of 48% inhibition was observed with a dose of 0.2 mg/kg/day (salt, equivalent to 0.13 mg/kg/day base) when administered orally and 12% inhibition when administered with the pumps.

The highest dose of 0.8 mg/kg/day (0.52 mg/kg/day base) reached a level of 42% inhibition with the ALZET® pumps and 79% by the oral administration.

When given by ALZET® pumps MAO-A inhibition in the brain was higher than the inhibition caused by oral administration. A dose of 0.2 mg/kg/day given orally caused 37% brain MAO-A inhibition when given orally and 57% inhibition when given by the pumps.

The dose of 0.8 mg/kg/day caused 78% by oral administration and 88% by the pumps.

When rasagiline was applied by pumps, hepatic MAO-A inhibition was higher than when given orally. Inhibition level of 71% was observed with dose of 0.2 mg/kg/day given by pumps, while when this dose was given orally, a level of 31% inhibition was observed.

Doses of 0.4 and 0.8 mg/kg/day caused full inhibition when given by pumps while only 54 and 70% respectively when administered per os (p.o.).

TABLE 1

MAO-B and MAO-A activity in different tissues, two weeks after rasagiline administration by continuous sc ALZET ® pumps or by oral administration (dpm +/− sd)

| rasagiline dose (salt) mg/kg/day | Intestine dpm + sd | | | | Brain dpm + sd | | | | Liver dpm + sd | | | |
|---|---|---|---|---|---|---|---|---|---|---|---|---|
| | MAO-B oral | MAO-B ALZET ® | MAO-A oral | MAO-A ALZET ® | MAO-B oral | MAO-B ALZET ® | MAO-A oral | MAO-A ALZET ® | MAO-B oral | MAO-B ALZET ® | MAO-A oral | MAO-A ALZET ® |
| saline | 14233 ± 1615 | 13206 ± 947 | 3668 ± 338 | 2955 ± 673 | 9103 ± 815 | 10305 ± 771 | 3665 ± 64 | 3764 ± 89 | 6782 ± 1494 | 5995 ± 797 | 2308 ± 216 | 2208 ± 82 |
| 0.02 | 3633 ± 275 | 8265 ± 2437 | 2712 ± 830 | 3199 ± 183 | 1586 ± 528 | 1229 ± 326 | 3441 ± 160 | 3479 ± 127 | 1127 ± 434 | 1974 ± 205 | 2127 ± 239 | 2192 ± 100 |
| 0.05 | 3115 ± 128 | 4346 ± 509 | 2607 ± 257 | 2831 ± 586 | 494 ± 60 | 346 ± 54 | 3031 ± 125 | 2974 ± 131 | 511 ± 160 | 912 ± 122 | 2199 ± 167 | 2185 ± 87 |
| 0.1 | 2493 ± 272 | 3225 ± 641 | 2308 ± 414 | 3029 ± 333 | 181 ± 38 | 198 ± 55 | 2822 ± 232 | 2595 ± 264 | 224 ± 28 | 486 ± 60 | 1963 ± 166 | 1930 ± 160 |
| 0.2 | 2424 ± 227 | 2391 ± 174 | 1891 ± 202 | 2604 ± 490 | 69 ± 16 | 75 ± 16 | 2319 ± 264 | 1613 ± 107 | 136 ± 85 | 312 ± 142 | 1582 ± 117 | 646 ± 898 |
| 0.4 | 2108 ± 257 | 1852 ± 225 | 1194 ± 216 | 1937 ± 404 | 34 ± 9 | 38 ± 10 | 1417 ± 147 | 917 ± 128 | 38 ± 6 | 181 ± 49 | 1058 ± 224 | 27 + 23 |
| 0.8 | 2105 ± 290 | 1879 ± 330 | 785 ± 41 | 1708 ± 212 | 9 ± 6 | 12 ± 12 | 803 ± 120 | 466 ± 42 | −5 ± 38 | 166 ± 46 | 681 ± 131 | 4 ± 15 |

TABLE 2

Percent of MAO-B and MAO-A inhibition in different tissues, two weeks after rasagiline administration continuously by sc ALZET ® pumps or by oral administration.

| rasagiline dose (salt) mg/kg/day | intestine | | | | Brain | | | | liver | | | |
|---|---|---|---|---|---|---|---|---|---|---|---|---|
| | MAO-B oral | MAO-B ALZET ® | MAO-A oral | MAO-A ALZET ® | MAO-B oral | MAO-B ALZET ® | MAO-A oral | MAO-A ALZET ® | MAO-B oral | MAO-B ALZET ® | MAO-A oral | MAO-A ALZET ® |
| 0.02 | 74 | 37 | 26 | −8 | 83 | 88 | 6 | 8 | 83 | 67 | 8 | 1 |
| 0.05 | 78 | 67 | 29 | 1 | 95 | 97 | 15 | 21 | 92 | 85 | 5 | 1 |
| 0.1 | 82 | 76 | 37 | −3 | 98 | 98 | 23 | 31 | 97 | 92 | 18 | 13 |
| 0.2 | 83 | 82 | 48 | 12 | 99 | 99 | 37 | 57 | 98 | 95 | 31 | 71 |
| 0.4 | 85 | 86 | 67 | 34 | 100 | 100 | 61 | 76 | 99 | 97 | 54 | 99 |
| 0.8 | 85 | 86 | 79 | 42 | 100 | 100 | 78 | 88 | 100 | 97 | 70 | 100 |

CONCLUSIONS

The inhibition levels of MAO-A in the intestine were lower when rasagiline was administered continuously with the subcutaneous pumps compared with oral administration, Administration of rasagiline by systemic subcutaneous ALZET® osmotic pumps, for 14 days, reduced the amount of Rasagiline reaching the gut, a fact which was expressed in reduced values of MAOA inhibition in this organ, as compared to values of MAOA inhibition obtained by oral administration. These differences were statistically significant. The lower MAOA inhibition in the intestine in the ALZET® pump group indicates a diminished danger for tyramine induced hypertension.

Unexpectedly, hepatic MAO-A inhibition was higher when rasagiline was given by the subcutaneous ALZET® osmotic pumps than when given orally.

In the brain, MAO inhibition by rasagiline administered by the subcutaneous ALZET® osmotic pumps was higher than that exerted by oral administration. Inhibition of MAOA in the brain to levels over 50% may cause in addition to some benefits in depression and other CNS functions, serotonin syndrome in depressed parkinsonian patients being treated concomitantly with selective serotonin uptake inhibitors (SSRIs). One treatment for serotonin syndrome is the administration of serotonin antagonists.

No change in MAOB inhibition in the brain between the two experimental groups has been observed. However, in the intestine and liver, MAOB inhibition by rasagiline administered by the subcutaneous ALZET® osmotic pumps was lower than that exerted by oral administration when rasagiline was administered daily at a dose of up to 0.1 mg/kg.

These results suggest the use of subcutaneous ALZET® osmotic pumps for the delivery of rasagiline.

In particular, based on the results obtained in the experiments described herein, controlled release parenteral formulations of rasagiline are effective to treat diseases such as premotor Parkinson's Disease. Patients with Parkinson's disease often experience symptoms such as autonomic dysfunction and impaired olfaction before the onset of motor symptoms. This stage of Parkinson's is also known as premotor Parkinson's Disease. Siderowf, A. and Stern, M. B. (2008), Premotor Parkinson's disease: Clinical features, detection, and prospects for treatment. Ann Neurol., 64: S139-S147. doi: 10.1002/ana.21462.

The best results were observed at 0.1 mg/kg rasagiline which corresponds to 1 mg clinical human dose. However, by increasing the dose from 0.2 to 0.8 mg/kg, the MAOA inhibitory values in the intestine remained low (below the 50% inhibition level), but a gradual increase in the inhibitory effect of rasagiline on MAOA in the brain occurred, reaching 57% at 0.2 mg/kg, 76% at 0.4 mg/kg and 88% at 0.8 mg/kg rasagiline. It seems, therefore, that the benefit of systemic administration by subcutaneous ALZET® osmotic pumps is present only at a certain narrow dose range of Rasagiline, which culminated approximately at 0.1 mg/kg. Beyond 0.1 mg/kg, starting at 0.2 mg/kg, the MAOA inhibition in the brain reaches 57% and is increased further to 76% and 88% with the higher doses of 0.4 and 0.8 mg/kg rasagiline, respectively. As mentioned previously, this may cause serotonin syndrome in patients receiving SSRIs.

Higher doses of rasagiline administered parenterally could also potentially lead to excess rasagiline in the liver. MAOA inhibition in the liver reached 71%, 99% and 100% at 0.2, 0.4 and 0.8 mg/kg dosages of rasagiline, respectively.

What is claimed is:

1. A method of preferentially inhibiting monoamine oxidase A (MAOA) in the brain of a subject in need of rasagiline therapy, relative to in the intestine of the subject comprising parenterally administering to the human subject a controlled released formation comprising a therapeutically effective amount of rasagiline or a pharmaceutically acceptable salt thereof, wherein the human subject in need of rasagiline therapy is a human subject afflicted with attention deficit hyperactivity disorder (ADHD), bipolar disorder, depression, post-traumatic stress disorder (PTSD), multiple system atroply (MSA) Progressive Supranuclear Palsy (PSP), restless legs syndrome, hearing loss, glaucoma, olfactory dysfunction, Parkinson's Disease, Multiple Sclerosis (MS), Alzheimer's Disease, Amyotrophic Lateral Sclerosis (ALS) or Huntington's Disease (HD).

2. The method of claim 1, wherein the therapeutically effective amount of rasagiline or a pharmaceutically acceptable salt thereof is delivered substantially entirely into the bloodstream of the human subject so as to reduce or avoid intestinal inhibition of MAOA while enhancing MAOA inhibition in the brain of the human subject.

3. The method of claim 1, wherein rasagiline is rasagiline base.

4. The method of claim 1, wherein the pharmaceutically acceptable salt is citrate, tannate, malate, mesylate, maleate, fumarate, tartrate, esylate, p-toluenesulfonate, benzoate, acetate, phosphate or sulfate.

5. The method of claims 1, wherein the percentage of MAOA inhibition in the brain is at least 5% higher than for a corresponding oral dose.

6. The method of claim 1, wherein the percentage of MAOA inhibition in the brain is at least 10% higher than the percentage of MAOA inhibition in the intestine.

7. The method of claim 1, wherein the controlled release formulation is a subcutaneous osmotic pump.

8. The method of claim 1, wherein the controlled release formulation releases rasagiline or a pharmaceutically acceptable salt thereof at a rate of 0.25µl/hr-10.0 µl/hr.

9. The method of claim 8, wherein the controlled release formulation releases rasagiline or a pharmaceutically acceptable salt thereof at a rate of about 0.5 µl/hr.

10. The method of claim 1, wherein the controlled release formulation comprises rasagiline at a daily dosage of 0.003 mg/kg-0.13 mg/kg.

11. The method of claim 10, wherein the controlled release formulation releases rasagiline at a daily dosage of about 0.016 mg/kg.

12. The method claim 1, wherein the subject in need of rasagiline therapy is a subject afflicted with restless legs syndrome, hearing loss, glaucoma, or olfactory dysfunction.

13. The method of claim 1, wherein the subject in need of rasagiline therapy is a subject afflicted with Parkinson's Disease, Multiple Sclerosis (MS), Alzheimer's Disease, Amyotrophic Lateral Sclerosis (ALS) or Huntington's Disease (HD).

14. The method of claim 1, wherein the controlled release formulation contains a total amount of rasagiline for a course of therapy lasting 1 week to 6 months.

15. A method of treating a human subject in need of rasagiline therapy comprising parenterally administering to the human subject a controlled release formulation comprising a therapeutically effective amount of rasagiline or a pharmaceutically acceptable salt thereof, so as to thereby treat the human subject, wherein the human subject in need of rasagiline therapy is a human subject afflicted with attention deficit hyperactivity disorder (ADHD), bipolar disorder, depression, post-traumatic stress disorder (PTSD), multiple system atrophy (MSA) Progressive Supranuclear Palsy (PSP), restless legs syndrome, hearing loss, glaucoma, olfactory dysfunction, Parkinson's Disease, Multiple Sclerosis (MS), Alzheimer's Disease, Amyotrophic Lateral Sclerosis (ALS) or Huntington's Disease (HD).

16. The method of claim 15, wherein rasagiline is rasagiline base.

17. The method of claim 15, wherein the pharmaceutically acceptable salt is citrate, tannate, malate, mesylate, maleate, fumarate, tartrate, esylate, p-toluenesulfonate, benzoate, acetate, phosphate or sulfate.

18. The method of claim 15, wherein the human subject in need of rasagiline therapy is a human subject afflicted with premotor Parkinson's Disease.

19. The method of claim 15, wherein the human subject in need of rasagiline therapy is a human subject afflicted with depression.

* * * * *